United States Patent
Beebe et al.

(10) Patent No.: US 12,403,477 B2
(45) Date of Patent: Sep. 2, 2025

(54) METHOD AND DEVICE FOR CREATING ORGANOTYPIC LUMEN MODELS IN A MICROWELL PLATE

(71) Applicant: Wisconsin Alumni Research Foundation, Madison, WI (US)

(72) Inventors: David J. Beebe, Monona, WI (US); Patrick H. McMinn, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 18/741,450

(22) Filed: Jun. 12, 2024

(65) Prior Publication Data

US 2024/0367174 A1    Nov. 7, 2024

Related U.S. Application Data

(62) Division of application No. 17/004,268, filed on Aug. 27, 2020, now Pat. No. 12,151,244.

(51) Int. Cl.
*B01L 3/00* (2006.01)
*B29C 39/02* (2006.01)
*B29L 31/40* (2006.01)

(52) U.S. Cl.
CPC ............ *B01L 3/5085* (2013.01); *B29C 39/02* (2013.01); *B01L 2200/12* (2013.01); *B01L 2300/0858* (2013.01); *B01L 2300/0893* (2013.01); *B01L 2300/12* (2013.01); *B29K 2995/0008* (2013.01); *B29L 2031/40* (2013.01)

(58) Field of Classification Search
CPC ................ B01L 2300/0858; B01L 2200/12
See application file for complete search history.

*Primary Examiner* — Natalia Levkovich
(74) *Attorney, Agent, or Firm* — Boyle Fredrickson, S.C.

(57) ABSTRACT

A method and device of creating a lumen model in a microwell plate defining a well is provided. A rod is inserted through the well of the microwell plate and the well is filled with a polymerizable material. The material is polymerized in the well. The rod is removed from the well of the microwell plate such that the polymerized material defines a lumen.

11 Claims, 9 Drawing Sheets

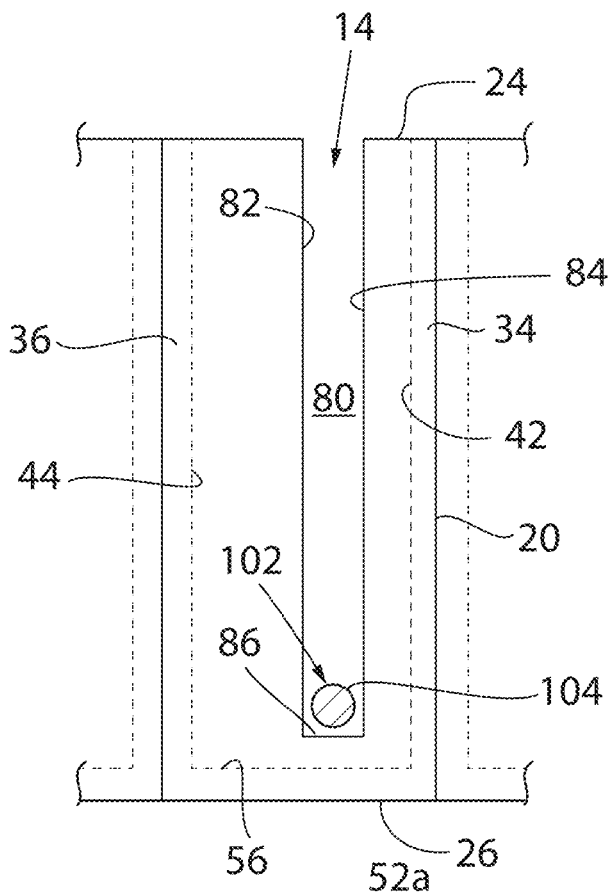
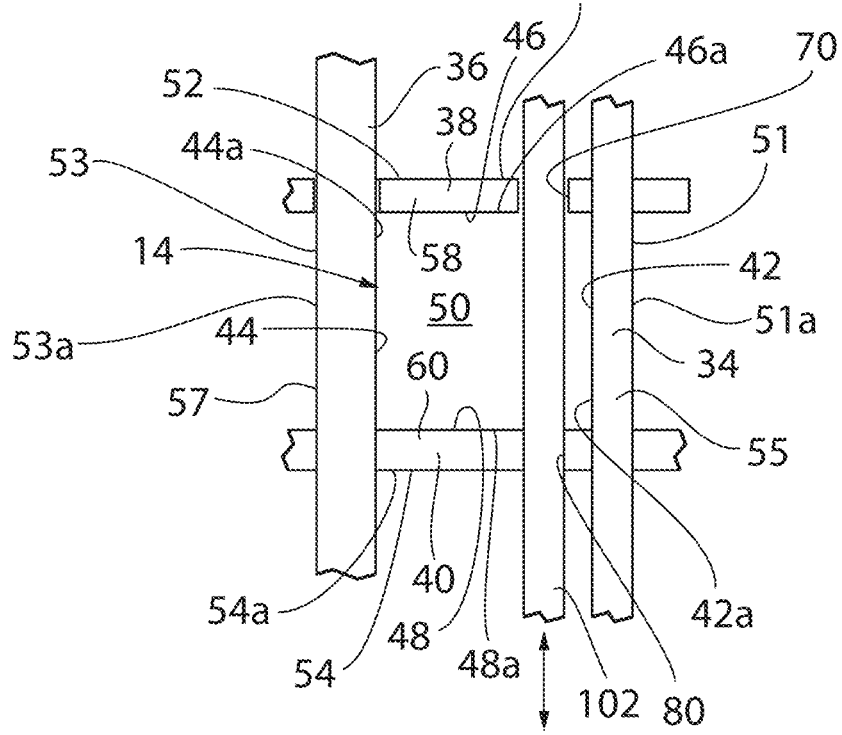
FIG. 2
FIG. 3

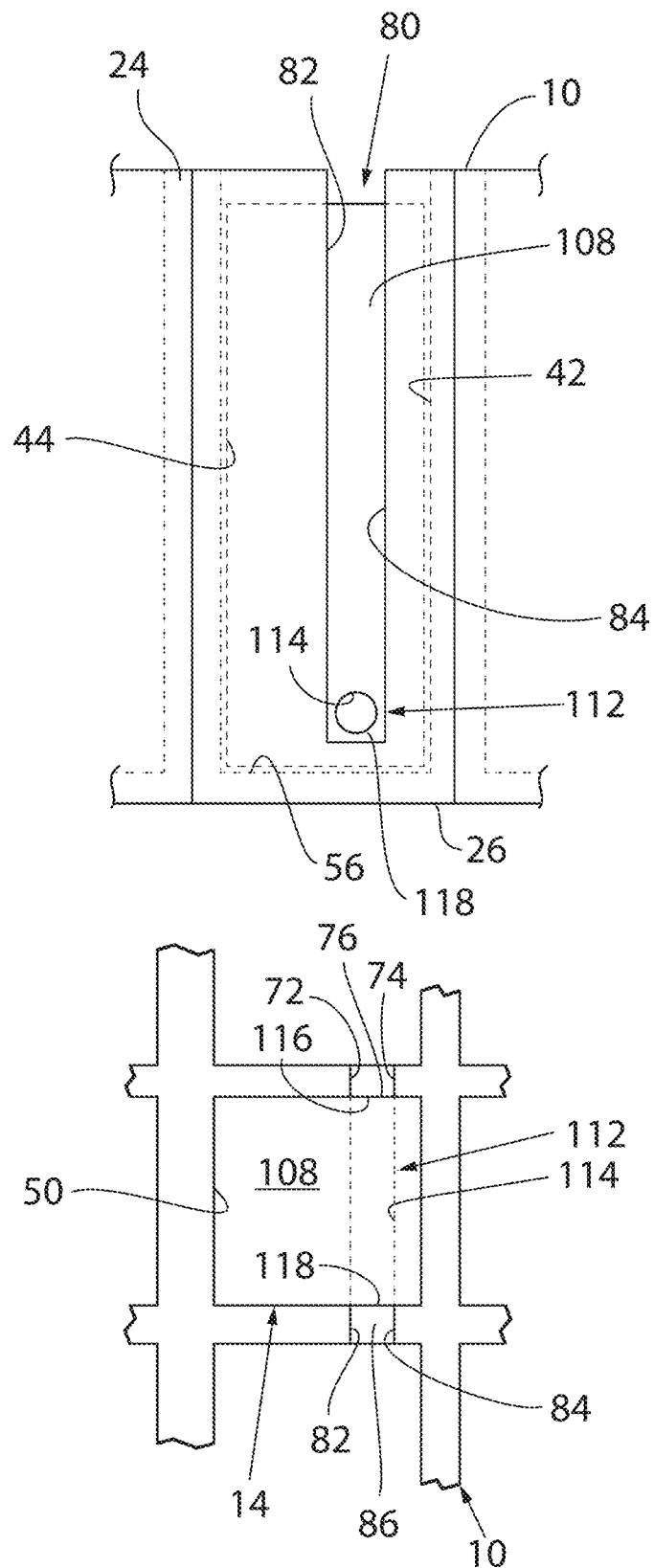

METHOD AND DEVICE FOR CREATING ORGANOTYPIC LUMEN MODELS IN A MICROWELL PLATE

CROSS REFERENCE TO RELATED APPLICATIONS

This application is a division of U.S. application Ser. No. 17/004,268, filed Aug. 27, 2020, the entirety of which is incorporated herein by reference.

FIELD OF THE INVENTION

This invention relates generally to microfluidics, and in particular, to a method of creating organotypic lumen models in a microwell plate.

BACKGROUND AND SUMMARY OF THE INVENTION

Advances in modern healthcare in the last few decades have, in part, led to better quality of life and higher life expectancy worldwide. However, mortality due to communicable and non-communicable diseases, such as drug-resistant tuberculosis, cardiovascular diseases, and cancers, continues to rise. A concerted effort from multiple fronts is needed to lessen global disease burden, including better preventive care (e.g. lifestyle education), improved access to healthcare services, affordable medical diagnosis and treatment, and continued growth of biomedical research. In the context of biomedical research, developing relevant tissue and organ models to better understand the pathophysiology of human diseases is of great importance to therapeutic discovery and implementation.

Two-dimensional (2D) in vitro culture models have formed the cornerstone of biomedical research for more than a century. Despite their ease-of-use and high experimental tractability, these models fail to recapitulate the three-dimensional (3D) tissue- and organ-level structure-function relationships observed in vivo. These limitations have led to the development of 3D culture techniques, including cells embedded in or on top of natural or synthetic hydrogels. Continued innovation has also led to organotypic culture, wherein self-assembled cellular clusters or organoids better mimic organ-level physiology. Compared with 2D cell culture, 3D techniques enable deeper analysis of the molecular mechanisms governing the pathophysiology of different diseases and can be valuable preclinical tools for drug testing. Nonetheless, current 3D models remain limited in their ability to capture crosstalk between multiple cell types and mechanical cues in the microenvironment that contribute to cellular mechanotransduction (e.g. fluid shear stress), which are important factors in disease progression. Mouse models could be suitable alternatives as they provide physiologically relevant microenvironments. However, mouse models have low experimental tractability and the evolution of the xenografted disease could be mouse-specific rather than patient-specific5, questioning the validity of such models.

Microfluidic cell culture, i.e. the synergy of tissue engineering with microscale physics, has enabled the development of microphysiological systems or organs-on-chips. These systems enable multi-culture of different cell types at physiological length scales, generation of stable biochemical gradients, and controlled fluid transport, among other unique capabilities. Microphysiological systems have been used to mimic many human organ systems, including the heart, brain, kidney, liver, lung, pancreas, and circulation. Importantly, organs-on-chips have demonstrated utility for unraveling basic mechanisms of disease and for predicting patient response to drugs in the context of translational medicine.

Lumens are tubular structures that are pervasive throughout all body systems, forming blood vessels that regulate nutrient and waste exchange in tissues to mammary ducts for the production of milk to intestinal tracts for nutrient absorption. Lumens are, perhaps, the earliest 3D geometry to develop during the process of embryonic neural tube formation. In major diseases such as cancer, ductal dysfunction in the breast and prostate can initiate tumorigenesis, and in later stages, the conditioning of normal blood and lymphatic vessels to a tumor-associated phenotype enables the spread of cancer cells to secondary sites in the body. Similarly, the stiffening and narrowing of blood vessels in atherosclerotic vascular disease can lead to complications in major organs including the heart, brain and kidney. Therefore, the importance of capturing luminal geometry in disease models goes beyond aesthetics to mimicking in vivo structure-function relationships.

Therefore, it is a primary object and feature of the present invention to provide a method and device for creating lumen models in a microwell plate.

It is a further object and feature of the present invention to provide a method and device for creating lumen models in a microwell plate that may be automated so as to allow for high-throughput fabrication.

It is a still further object and feature of the present invention to provide a method and device for creating lumen models in a microwell plate that is simple and inexpensive to implement.

In accordance with the present invention, a method of creating a lumen model in a microwell plate defining a well is provided. The method includes the steps of inserting a rod through the well of the microwell plate and filling the well with a polymerizable material. The material in the well is polymerized and the rod is removed from the well of the microwell plate such that the polymerized material defines a lumen.

The rod may have a circular cross-section and may be magnetic or be fabricated from a polymer. The rod may be a first rod and the lumen may be a first lumen. As such, a second rod may be inserted through the well of the microwell plate and removed from the well of the microwell plate after the material in the well is polymerized such that the polymerized material defines a second lumen. The first and second lumens may be generally parallel or perpendicular. In addition, the first and second lumens may extend along corresponding axes that are axially spaced or the first lumen may communicate with the second lumen.

In accordance with a further aspect of the present invention, a method of creating a lumen model in a microwell plate defining a plurality of wells. Each of the plurality of wells is defined by at least one sidewall. The method includes the step of inserting at least one rod through first and second openings in each of the at least one sidewall defining the plurality of wells and through the plurality of wells. At least a portion of the plurality of wells are filled with a polymerizable material and the material is polymerized in the at least a portion of the plurality of wells. The at least one rod is removed from the first and second openings in each of the at least one sidewall defining the plurality of wells and from the plurality of wells such that the polymerized material in the at least a portion of the plurality of wells define first lumens in the at least a portion of the plurality of wells.

Third and fourth openings may be provided in each of the at least one sidewall defining the plurality of wells. The at least one rod may be inserted through third and fourth openings in each of the at least one sidewall defining the plurality of wells and through the plurality of wells. The at least one rod is removed from the third and fourth openings in each of the at least one sidewall defining the plurality of wells and from the plurality of wells such that the polymerized material in the at least a portion of the plurality of wells define second lumens in the plurality of wells. The first and second lumens in each well of the at least a portion of the plurality of wells may be generally parallel or generally perpendicular. In addition, the first and second lumens in each well of the at least a portion of the plurality of wells may extend along corresponding axes which are axially spaced. Further, the first lumen in each well of the at least a portion of the plurality of wells may communicate with the second lumen in each well of the at least a portion of the plurality of wells.

It is contemplated for the steps of inserting the at least one rod through the first and second openings in each of the at least one sidewall defining each well of the plurality of wells and through the plurality of wells and inserting the at least one rod through the third and fourth openings in each of the at least one sidewall defining each well of the plurality of wells and through the plurality of wells to occur simultaneously.

In accordance with a still further aspect of the present invention, a device is provided for creating a lumen in a microenvironment. The device includes a plurality of rods and a microwell plate defining a plurality of wells arranged in rows and columns. Each of the plurality of wells defined by at least one sidewall having first and second openings therein. Each rod is selectively moveable between a first position wherein each rod is removed from corresponding first and second openings in each of the at least one sidewall defining the plurality of wells and a second position wherein each rod is inserted through the corresponding first and second openings in each of the at least one sidewall defining the plurality of wells. A fixture is interconnected to the plurality of rods. The fixture is configured for moving the plurality of rods between the first and second positions.

Each of the plurality of rods may be parallel to each other. In addition, the at least one sidewall defining the plurality of wells has third and fourth openings therein. The plurality of rods may be a first plurality of rods and the device may include a second plurality of rods. Each rod of the second plurality of rods is selectively moveable between a first position wherein each rod of the second plurality of rods is removed from the third and fourth openings in each of the at least one sidewall defining the plurality of wells and a second position wherein each rod of the second plurality of rods is inserted through the third and fourth openings in each of the at least one sidewall defining the plurality of wells.

The fixture may be interconnected to the second plurality of rods. The fixture may be configured for moving the second plurality of rods between the first and second positions. Alternatively, the fixture may be a first fixture and the device may include a second fixture interconnected to the second plurality of rods. The second fixture is configured for moving the second plurality of rods between the first and second positions.

The first plurality of rods may lie in a first plane and the second plurality of rods may lie in a second plane spaced from the first plane. The first plurality of rods may be parallel or transverse to the second plurality of rods. Each of the first plurality of rods travels along a path between the first and second positions of the first plurality of rods and each of the second plurality of rods travels along a path between the first and second positions of the second plurality of rods. The path of each of the first plurality of rods is interested by the paths of the second plurality of rods.

Each of the plurality of rods may have a circular cross-section. In addition, each of the plurality of rods may magnetic or may be fabricated from a polymer.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 2 is a cross-sectional view of the system of the present invention taken along line 2-2 of FIG. 1;

FIG. 3 is a top plan view of the system of FIG. 3;

FIG. 4 is a cross-sectional view of the system of the present invention, similar to FIG. 2, showing a lumen model fabricated in the microwell plate;

FIG. 5 is a top plan view of the system of the present invention, similar to FIG. 3, showing a lumen model fabricated in the microwell plate;

DETAILED DESCRIPTION OF THE DRAWINGS

Figure 1:
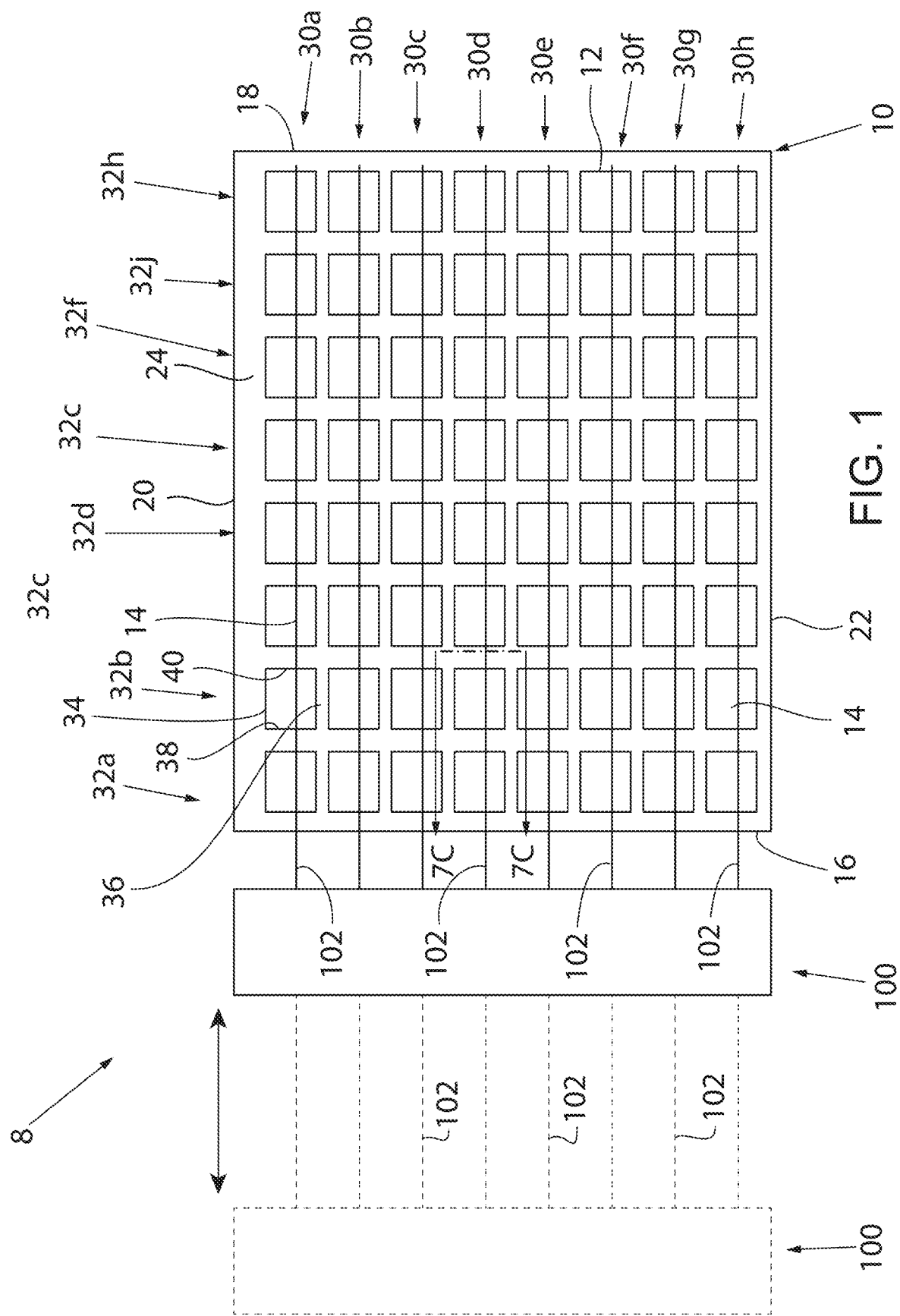
FIG. 1 is schematic view of a system for effectuating a methodology of fabricating lumen models in a microwell plate in accordance with the present invention.

Referring to FIGS. 1-5, a system for effectuating the methodology of the present invention is generally designated by the reference numeral 5. System 5 includes well plate 10 fabricated from a plastic material such as polyvinylchloride, polystyrene or polypropylene and has a generally rectangular configuration. However, other configurations are possible without deviating from the scope of the present invention. Well plate 10 is defined by first and second generally parallel ends 16 and 18, respectively, interconnected first and second generally parallel sidewalls 20 and 22, respectively, perpendicular thereto. Well plate 10 further includes an upwardly directed surface 24 and a downwardly directed surface 26. A plurality of wells, designated collectively by the reference numeral 12, are provided in upper surface 24 of well plate 10. By way of example, in the depicted embodiment, well plate 10 includes sixty four (64) individual wells 14 arranged in eight (8) rows 30a-30h and eight (8) columns 32a-32h. However, it can be understood that the number and arrangement of wells 14 in well plate 10 may be varied, without deviating from the scope of the present invention.

Each well 14 in upper surface 24 of well plate 10 is identical in structure. As such, the description hereinafter of well 14 located at the intersection of row 30d and column 32b is understood to described each of the plurality of wells 12, as if fully described herein. Well 14 at the intersection of row 30d and column 32b is defined first and second generally parallel sidewalls 34 and 36, respectively, generally parallel to first and second sides 20 and 22, respectively, of well plate 10 and generally perpendicular to first and second ends 16 and 18, respectively, of well plate 10 and by third and fourth generally parallel sidewalls 38 and 40, respectively, generally perpendicular to first and second sides 20 and 22, respectively, of well plate 10 and generally parallel to first and second ends 16 and 18, respectively, of well plate 10. First face 42 of first sidewall 34, first face 44 of second sidewall 36, first face 46 of third sidewall 38 and first face 48 of fourth sidewall 40 are directed toward interior 50 of well 14. Lower edges of first face 42 of first sidewall 34, first face 44 of second sidewall 36, first face 46 of third sidewall 38 and first face 48 of fourth sidewall 40 are interconnected by lower wall 56.

It can be understood that second face 51 of first sidewall 34 defines a corresponding first face 44 of second sidewall 36 in an adjacent well 14 in the same column, e.g. well 14 at row 30c, column 32b. Similarly, second face 53 of second sidewall 36 defines a corresponding first face 42 of first sidewall 34 in an adjacent well 14 in the same row, e.g. well 14 at row 30e, column 32c. Upper face 55 of first sidewall 34 extends between and interconnects upper edge 42a of first face 42 of first sidewall 34 and upper edge 51a of second face 51 of first sidewall 34. Upper face 57 of second sidewall 44 extends between and interconnects upper edge 44a of first face 44 of second sidewall 36 and upper edge 53a of second face 53 of second sidewall 36.

Further, second face 52 of third sidewall 38 defines a corresponding first face in an adjacent well 14, e.g. well 14 at row 30a, column 32a. Similarly, second face 54 of fourth sidewall 40 defines a corresponding first face in an adjacent well 14, e.g. well 14 at row 30a, column 32c. Upper face 58 of third sidewall 38 extends between and interconnects upper edge 46a of first face 46 of third sidewall 38 and upper edge 52a of second face 52 of third sidewall 38. Upper face 60 of fourth sidewall 40 extends between and interconnects upper edge 48a of first face 48 of fourth sidewall 40 and upper edge 54a of second face 54 of fourth sidewall 40. It is noted that upper face 55 of first sidewall 34, upper face 57 of second sidewall, upper face 58 of third sidewall 38 and upper face 60 of fourth sidewall 40 are co-planer and partially define upper surface 24 of well plate 10.

As best seen in FIG. 5, first rod receiving slot 70 is provided in upper face 58 of third sidewall 38. Rod receiving slot 70 is defined by first and second generally parallel sidewalls 72 and 74, respectively, spaced from each other and extending between first and second faces 46 and 52, respectively, thereof. First and second sidewalls 72 and 74, respectively, terminate at and are interconnected by lower surface 76 spaced from and parallel to lower wall 56. Lower surface 76 is generally perpendicular to first and second sidewalls 72 and 74, respectively, and extends between first and second faces 46 and 52, respectively, of third sidewall 38.

Similarly, referring to FIGS. 4-5, second rod receiving slot 80 is provided in upper face 60 of fourth sidewall 40. As hereinafter described, it is intended for second rod receiving slot 80 to axially aligned with and have an identical configuration to first rod receiving slot 70. More specifically, second rod receiving slot 80 is defined by first and second generally parallel sidewalls 82 and 84, respectively, spaced from each other and extending between first and second faces 48 and 54, respectively, thereof. First and second sidewalls 82 and 84, respectively, terminate at and are interconnected by lower surface 86 spaced from and parallel to lower wall 56. Lower surface 86 is generally perpendicular to first and second sidewalls 82 and 84, respectively, and extends between first and second faces 48 and 54, respectively, of fourth sidewall 40. It is intended for lower surfaces 76 and 86 partially defining corresponding first and second rod receiving slots 70 and 80, respectively, to be co-planar and to define a lower limit as to the vertical spacing between lower wall 56 and the lumen model, hereinafter described.

System 5 further includes fixture 100 to support and move a plurality of identical, parallelly extending rods 102, as hereinafter described. It is for the plurality of rods 102 to be magnetic to facilitate the connection of the plurality of rods 102 to fixture 100. However, the plurality of rods may be fabricated from other materials without deviating from the scope of the present invention. The plurality of rods 102 are spaced such that each rod 102 is axially aligned with a corresponding row 30a-30h of wells 14 in well plate 10. Each of the plurality of rods 102 has an outer surface 104 and a generally circular cross-section. It is intended for fixture 100 to simultaneously move the plurality of rods 102 axially from a first retracted position, shown in phantom in FIG. 1, wherein the plurality of rods 102 are removed from well plate 10, and second extended position wherein each rod 102 extends through first and second rod receiving slots 70 and 80, respectively, in third and fourth sidewalls 38 and 40, respectively, defining each well 14 in a corresponding row 30a-30h of wells 14 in well plate 10, FIGS. 1-3.

In operation, with the plurality of rods 102 in the first retracted position, fixture 100 and well plate 10 are aligned such that each rod 102 of the plurality of rods 102 in axially aligned with first and second rod receiving slots 70 and 80, respectively, in third and fourth sidewalls 38 and 40, respectively, defining each well 14 in a corresponding row 30a-30h of wells 14 in well plate 10. Thereafter, the plurality of rods 102 are moved from the first retracted position to the second extended position wherein each rod 102 extends through first and second rod receiving slots 70 in third and fourth sidewalls 38 and 40, respectively, defining each well 14 in a corresponding row 30a-30h of wells 14 in well plate 10.

Referring back to FIGS. 4-5, unpolymerized, polymerizable material 108, e.g. a synthetic hydrogel, is deposited into interiors 50 of all of or a portion of wells 14 in well plate 10, e.g., wells 14 in columns 32b and 32f of well plate 10 in any conventional manner, such as by pipetting. With polymerizable material 108 deposited into interiors 50 of wells 14 in columns 32b and 32f of well plate 10, a predetermined stimulus, e.g., heat or light, is directed at material 108 in interiors 50 of wells 14 in columns 32b and 32f of well plate 10 such that material 108 in the interiors 50 of wells 14 in columns 32b and 32f is polymerized. With material 108 in the interior 50 of wells 14 in columns 32b and 32f polymerized, fixture 100 retracts the plurality of rods 102 from the polymerized material 108 in interior 50 of wells 14 in columns 32b and 32f, such that a lumen model or generally tubular passageway 112 extends through polymerized material 108 extending between third and fourth sidewalls 38 and 40, respectively. Tubular passageway 112 is defined by tubular surface 114 of polymerized material 108 and includes a first opening 116 communicating with first rod receiving slot 70 in third sidewall 38 and a second opening communicating with second rod receiving slot 80 in fourth sidewall 40.

It can be understood that a first media, which may include cells, molecules or the like, may be deposited in a well, e.g., well 14 at row 30d, column 32a, adjacent to a corresponding well, e.g., well 14 at row 30d, column 32b, having tubular passageway 112 extending through polymerized material 108 therein. The first media in well 14 at row 30d, column 32a communicates with first opening 116 through first rod receiving slot 70 in third sidewall 38 of well 14 at row 30d, column 32b. As such, the first media travels through first opening 116, tubular passageway 112, second opening 118 and second rod receiving slot 80 in fourth sidewall 40 into well 14, e.g., at row 30d, column 32c, adjacent thereto by means of gravity, a mechanical device or the like.

Similarly, a second media, which may include cells, molecules or the like, may be deposited in a well, e.g., well 14 at row 30d, column 32e, adjacent to a corresponding second well, e.g., well 14 at row 30d, column 32f, having tubular passageway 112 extending through polymerized material 108 therein. The second media in well 14 at row 30d, column 32e communicates with first opening 116 through first rod receiving slot 70 in third sidewall 38 well 14 at row 30d, column 32f. As such, the second media travels through first opening 116, tubular passageway 112, second opening 118 and second rod receiving slot 80 in fourth sidewall 40 into well 14, e.g., at row 30d, column 32g, adjacent thereto by means of gravity, a mechanical device or the like.

In can be appreciated that utilizing the same methodology heretofore described, the same or different media may be flowed through each tubular passageway 112 extending through the portion of the plurality of wells 14 having polymerized material 108 therein, thereby allowing a user to run multiple tests and/or experiments simultaneously. It is noted that wells 14, e.g., wells 14 in column 30d, may be used to isolate and separate the portion of the plurality of wells 14 having polymerized material 108 therein from each other and from the media introduced therein.

Referring to FIGS. 6-11, it is contemplated to provide additional lumen models or generally tubular passageways through polymerized material 108. More specifically, third rod receiving slot 120 is provided in upper face 55 of first sidewall 34. Third rod receiving slot 120 is defined by first and second generally parallel sidewalls 122 and 124, respectively, spaced from each other and extending between first and second faces 42 and 51, respectively, first sidewall 34. First and second sidewalls 122 and 124, respectively, terminate at and are interconnected by lower surface 126 spaced from and parallel to lower wall 56. Lower surface 126 is generally perpendicular to first and second sidewalls 122 and 124, respectively, and extends between first and second faces 42 and 51, respectively, of first sidewall 34.

Similarly, fourth rod receiving slot 130 is provided in upper face 57 of second sidewall 36. For reasons hereinafter described, it is intended for fourth rod receiving slot 130 to axially aligned with and have an identical configuration to third rod receiving slot 120. More specifically, fourth rod receiving slot 130 is defined by first and second generally parallel sidewalls 132 and 134, respectively, spaced from each other and extending between first and second faces 44 and 53, respectively, of second sidewall 36. First and second sidewalls 132 and 134, respectively, terminate at and are interconnected by lower surface 136 spaced from and parallel to lower wall 56. Lower surface 136 is generally perpendicular to first and second sidewalls 132 and 134, respectively, and extends between first and second faces 44 and 53, respectively, of second sidewall 36. It is intended for lower surfaces 126 and 136 defining partially defining third and fourth rod receiving slots 120 and 130, respectively, to be co-planar and to define a lower limit as to the vertical spacing between lower wall 56 and the lumen model, as hereinafter described.

Figure 6:
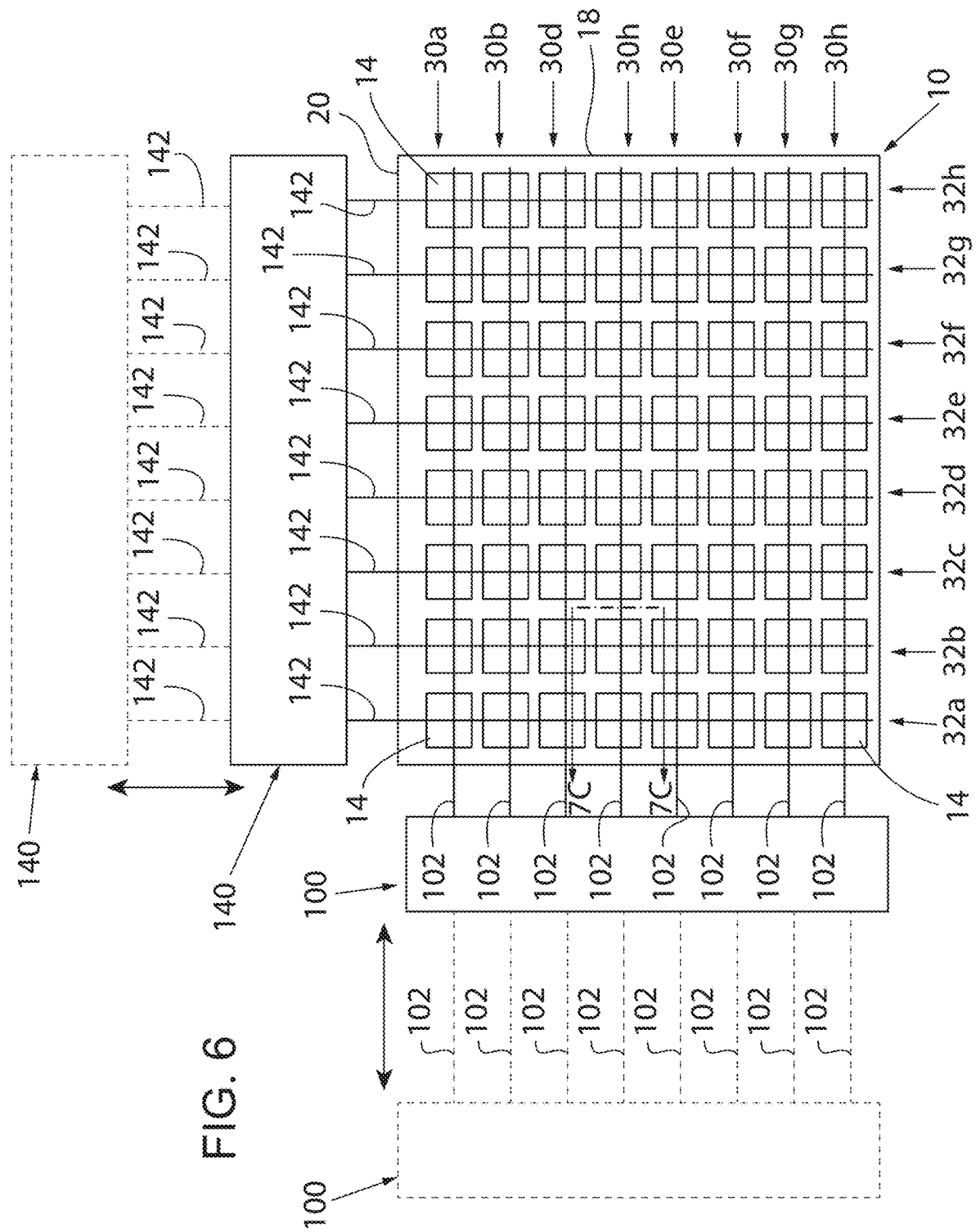
FIG. 6 is schematic view of an alternate configuration of a system for effectuating a methodology of fabricating lumen models in a microwell plate in accordance with the present invention.
Figure 7:
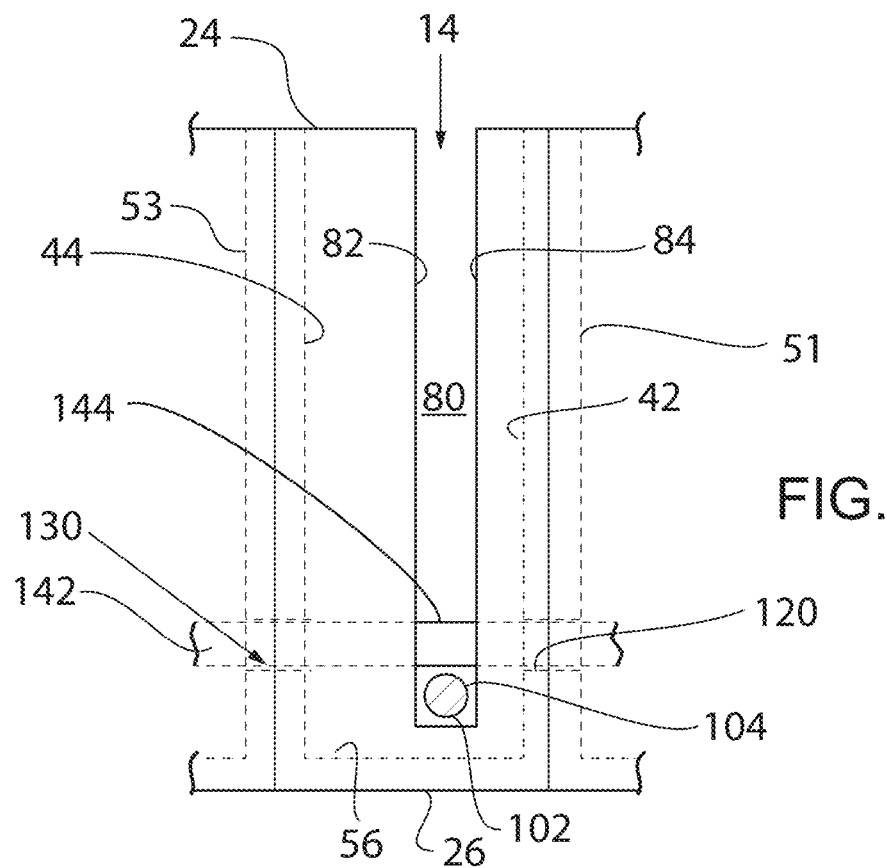
FIG. 7 is a cross-sectional view of the system of the present invention taken along line 7-7 of FIG. 6.
Figure 8:
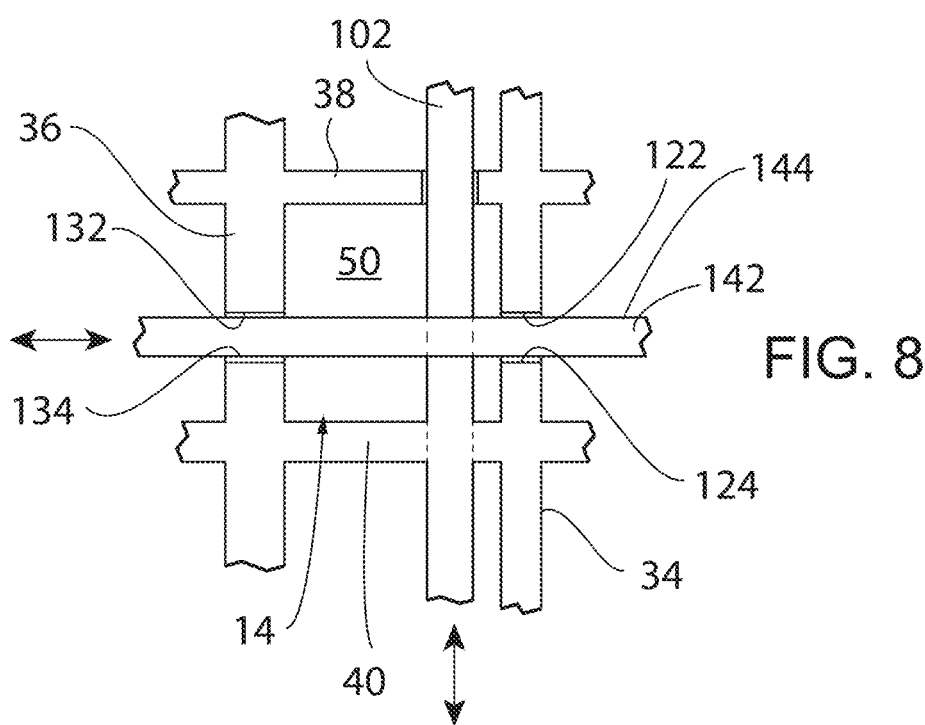
FIG. 8 is a top plan view of the system of FIG. 7.
Figure 9:
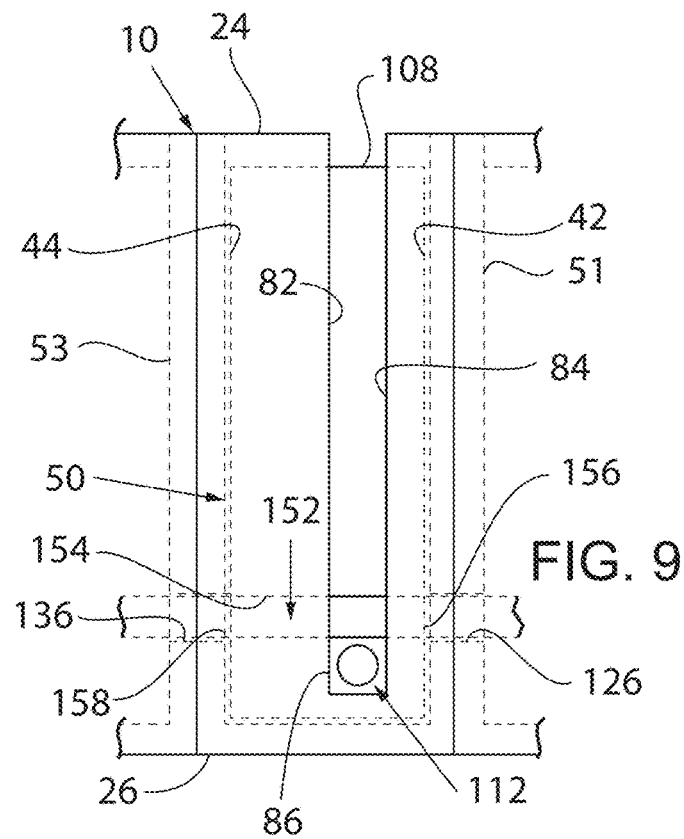
FIG. 9 is a cross-sectional view of the system of the present invention, similar to FIG. 7, showing first and second lumen models fabricated in the microwell plate.
Figure 11:
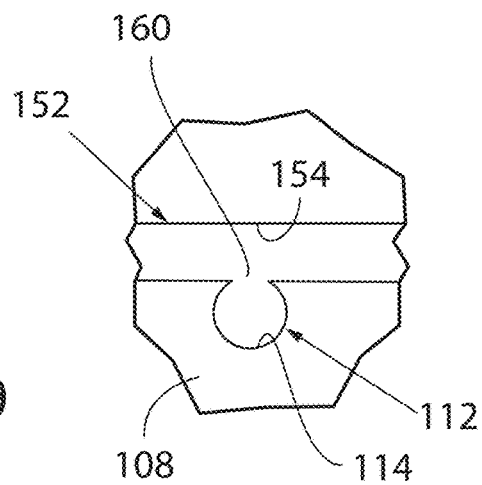
FIG. 11 is a cross-sectional view of the system of the present invention taken along line 11-11 of FIG. 10.
Figure 10:
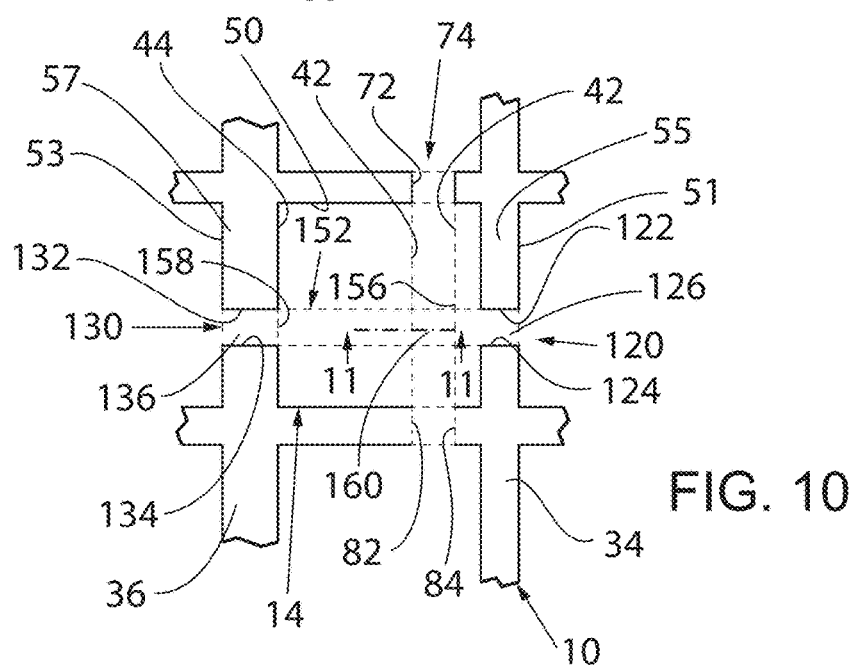
FIG. 10 is a top plan view of the system of the present invention, similar to FIG. 8, showing the first and second lumen models fabricated in the microwell plate.
Figure 12:
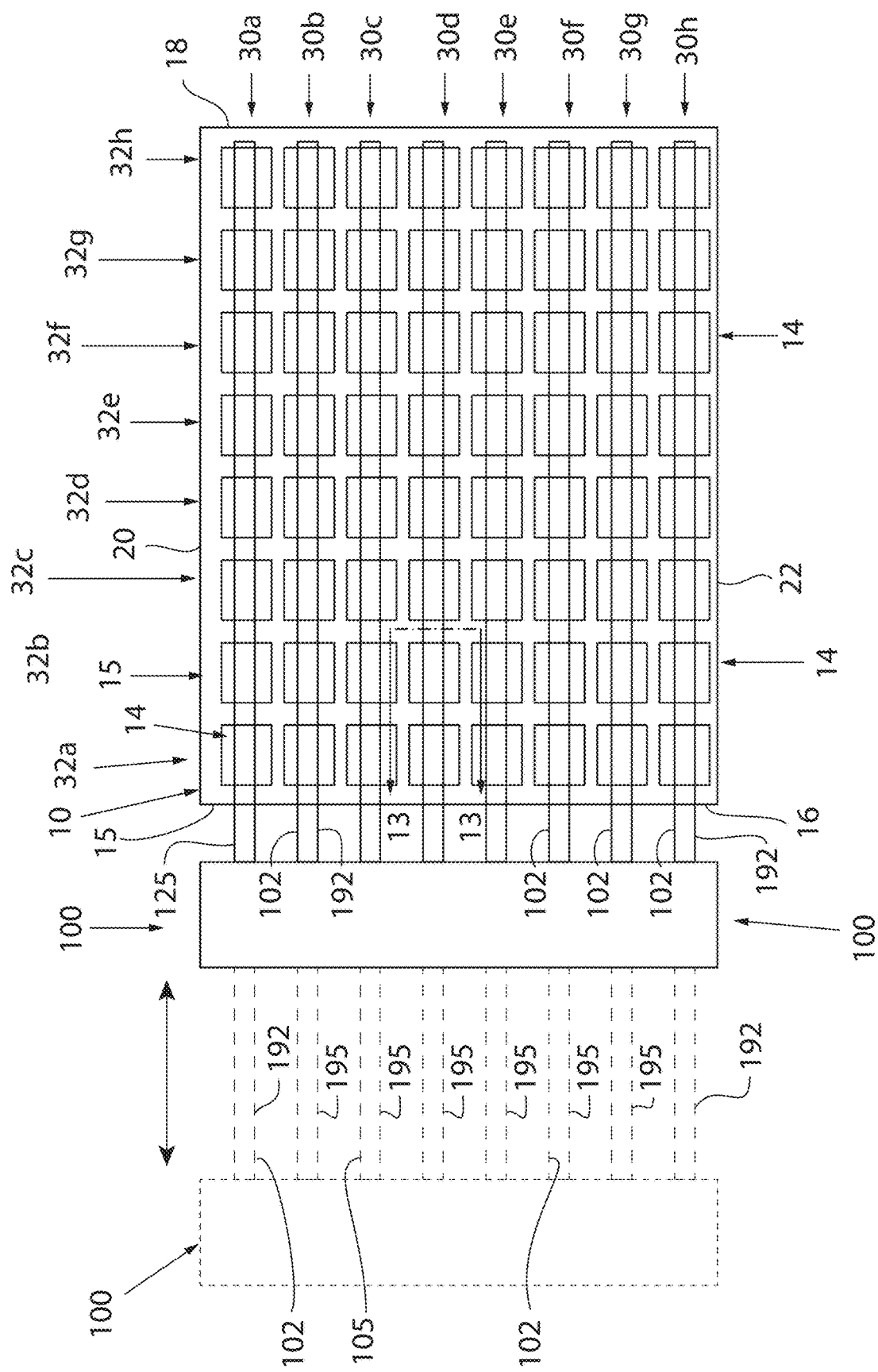
FIG. 12 is schematic view of a still further alternate configuration of a system for effectuating a methodology of fabricating lumen models in a microwell plate in accordance with the present invention.

System 5 may further include second fixture 140 supporting a second plurality of identical, parallelly extending rods 142, as hereinafter described, FIG. 6. It is for the plurality of rods 142 to be magnetic to facilitate the connection of the plurality of rods 142 to second fixture 140. However, the plurality of rods 142 may be fabricated from other materials without deviating from the scope of the present invention. The plurality of rods 142 are spaced such that each rod 142 is axially aligned with a corresponding columns 32a-32h of wells 14 in well plate 10. Each of the plurality of rods 142 has an outer surface 144 and a generally circular cross-section. It is intended for fixture 140 to simultaneously move the plurality of rods 142 axially from a first retracted position, shown in phantom in FIG. 6, wherein the plurality of rods 142 are removed from well plate 10, and second extended position wherein each rod 142 extends through third and fourth rod receiving slots 120 and 130, respectively, in first and second sidewalls 34 and 36, respectively, defining each well 14 in a corresponding column 32a-32h of wells 14 in well plate 10.

In operation, with the plurality of rods 102 and the plurality of rods 142 in the first retracted positions, fixture 100 and well plate 10 are aligned such that each rod 102 of the plurality of rods 102 in axially aligned with first and second rod receiving slots 70 and 80, respectively, in third and fourth sidewalls 38 and 40, respectively, defining each well 14 in a corresponding row 30a-30h of wells 14 in well plate 10. Similarly, second fixture 140 and well plate 10 are aligned such that each rod 142 of the plurality of rods 142 is axially aligned with third and fourth second rod receiving slots 120 and 130, respectively, in first and second sidewalls 34 and 36, respectively, defining each well 14 in a corresponding columns 32a-32h of wells 14 in well plate 10. It is noted that the plurality of rods 102 lie in a first plane parallel to and vertically spaced from a plane in which lower walls 56 of the plurality of wells 14 lie and the plurality of rods 142 lie in a second plane parallel to and vertically spaced from the first plane and from the plane in which lower walls 56 of the plurality of wells 14 lie, thereby allowing the plurality of rods 102 and the plurality of rods 142 to cross each other within the plurality of wells 14 of well plate 10 when the plurality of rods 102 and the plurality of rods 142 are moved to the second extended positions, FIGS. 7-8.

As heretofore described, the plurality of rods 102 are moved from the first retracted position to the second extended position wherein each rod 102 extends through first and second rod receiving slots 70 in third and fourth sidewalls 38 and 40, respectively, defining each well 14 in a corresponding row 30a-30h of wells 14 in well plate 10.

Similarly, the plurality of rods 142 are moved from the first retracted position to the second extended position wherein each rod 142 extends through third and fourth second rod receiving slots 120 and 130, respectively, in first and second sidewalls 34 and 36, respectively, defining each well 14 in a corresponding columns 32a-32h of wells 14 in well plate 10. In the depicted embodiment, the lower portions of each of the plurality of rods 142 engage corresponding upper portions of the plurality of rods 102 in each row 30a-30h within interiors 50 of wells 14 in each row 30a-30h of wells 14 in well plate 10.

Unpolymerized, polymerizable material 108, such as a synthetic hydrogel, is deposited into interior 50 of all or a portion of the plurality of wells 14 in well plate 10, e.g., via pipetting. For example, it is contemplated to provide unpolymerized, polymerizable material 108 in the interior 50 of well 14 at the intersection of row 30d with column 32b. Thereafter, a predetermined stimulus, e.g., heat or light, is directed at material 108 in the interior 50 of well 14 at the intersection of row 30d with column 32b such that material 108 in the interior 50 of well 14 at the intersection of row 30d with column 32b is polymerized. With material 108 in the interior 50 of well 14 at the intersection of row 30d with columns 32b polymerized, fixture 100 retracts the plurality of rods 102 from the polymerized material 108 in interior 50 of well 14 at the intersection of row 30d with column 32b such that a lumen model or generally tubular passageway 112, as heretofore described, extends through polymerized material 108 between third and fourth sidewalls 38 and 40, respectively. Similarly, second fixture 140 retracts the plurality of rods 142 from the polymerized material 108 in interior 50 of well 14 at the intersection of row 30d with column 32b such that a lumen model or generally tubular passageway 152 extends through polymerized material 108 between first and second sidewalls 34 and 36, respectively. Tubular passageway 152 is defined by tubular surface 154 of polymerized material 108 and includes a first opening 156 communicating with third rod receiving slot 120 in first sidewall 34 and a second opening 158 communicating with fourth rod receiving slot 130 in second sidewall 36. In the depicted embodiment, tubular passageways 112 and 152 communicate with each other at intersection 160, FIG. 11, and extend along axes generally perpendicular to each other. It can be appreciated the axes along which tubular passageways 112 and 152 extend may be vertically adjusted, and spaced from each other, by adjusting the vertical positions of the plurality of rods 102 and the plurality of rods 142, respectively.

It can be understood that a first media, which may include cells, molecules or the like, may be deposited in a well, e.g., well 14 at row 30d, column 32a, adjacent to a corresponding well, e.g., well 14 at row 30d, column 32b, having tubular passageway 112 extending through polymerized material 108 therein. As such, the first media travels through first opening 116, tubular passageway 112, second opening 118 and second rod receiving slot 80 in fourth sidewall 40 into well 14, e.g., at row 30d, column 32c, adjacent thereto by means of gravity, a mechanical device or the like.

Similarly, a second media, which may include cells, molecules or the like, may be deposited in a well, e.g., well 14 at row 30c, column 32b, adjacent to a corresponding well 14 at row 30d, column 32b, having tubular passageway 112 extending through polymerized material 108 therein. As such, the second media travels through first opening 156, tubular passageway 152, second opening 158 and fourth rod receiving slot 130 in second sidewall 36 into well 14 at row 30e, column 32b, adjacent thereto by means of gravity, a mechanical device or the like. It can appreciated that the first and second media may communicate with each other through intersection 160 of tubular passageways 112 and 152.

In can be appreciated that utilizing the same methodology heretofore described, the same or different media may be flowed through each tubular passageways 112 and 152 extending through the portion of the plurality of wells 14 having polymerized material 108 therein, thereby allowing a user to run multiple tests and/or experiments simultaneously.

In addition, referring to FIGS. 12-16, it is contemplated to provide additional lumen models or generally tubular passageways parallel to tubular passageway 112 in polymerized material 108. Fifth rod receiving slot 170 is provided in upper face 58 of third sidewall 38. Fifth rod receiving slot 170 is defined by first and second generally parallel sidewalls 172 and 174, respectively, spaced from each other and extending between first and second faces 46 and 52, respectively, thereof. First and second sidewalls 172 and 174, respectively, terminate at and are interconnected by lower surface 176 spaced from and parallel to lower wall 56. Lower surface 176 is generally perpendicular to first and second sidewalls 172 and 174, respectively, and extends between first and second faces 46 and 52, respectively, of third sidewall 38.

Similarly, sixth rod receiving slot 180 is provided in upper face 60 of fourth sidewall 40. As hereinafter described, it is intended for second rod receiving slot 180 to axially aligned with and have an identical configuration to first rod receiving slot 170. More specifically, sixth rod receiving slot 180 is defined by first and second generally parallel sidewalls 182 and 184, respectively, spaced from each other and extending between first and second faces 48 and 54, respectively, thereof. First and second sidewalls 182 and 184, respectively, terminate at and are interconnected by lower surface 186 spaced from and parallel to lower wall 56. Lower surface 186 is generally perpendicular to first and second sidewalls 182 and 184, respectively, and extends between first and second faces 48 and 54, respectively, of fourth sidewall 40. It is intended for lower surfaces 176 and 186 partially defining corresponding first and second rod receiving slots 170 and 180, respectively, to be co-planar and to define a lower limit as to the vertical spacing between lower wall 56 and the lumen model, hereinafter described.

Figure 13:
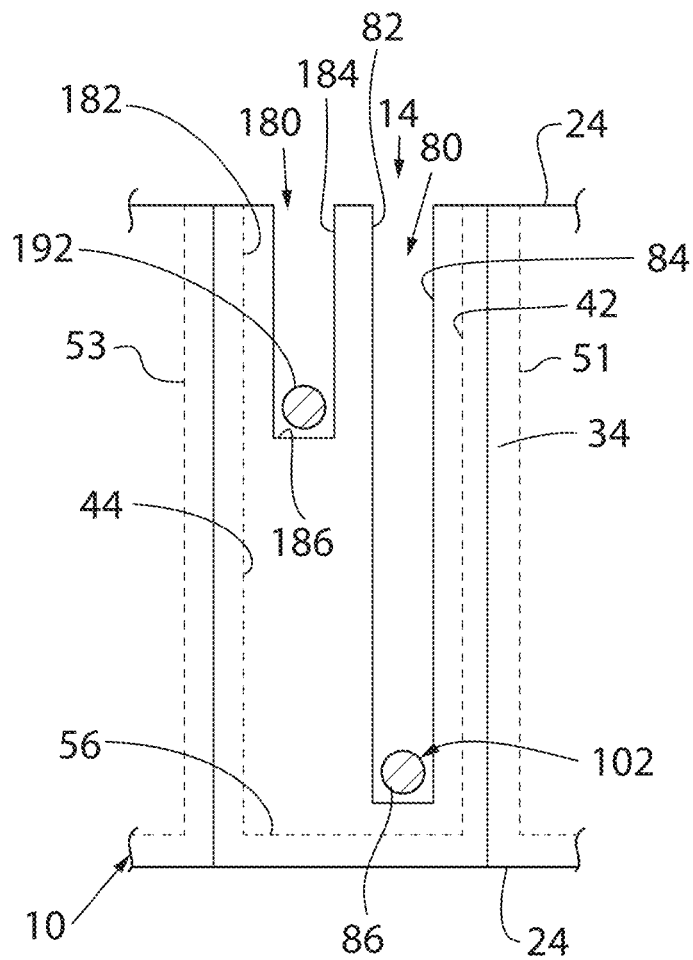
FIG. 13 is a cross-sectional view of the system of the present invention taken along line 13-13 of FIG. 12.
Figure 14:
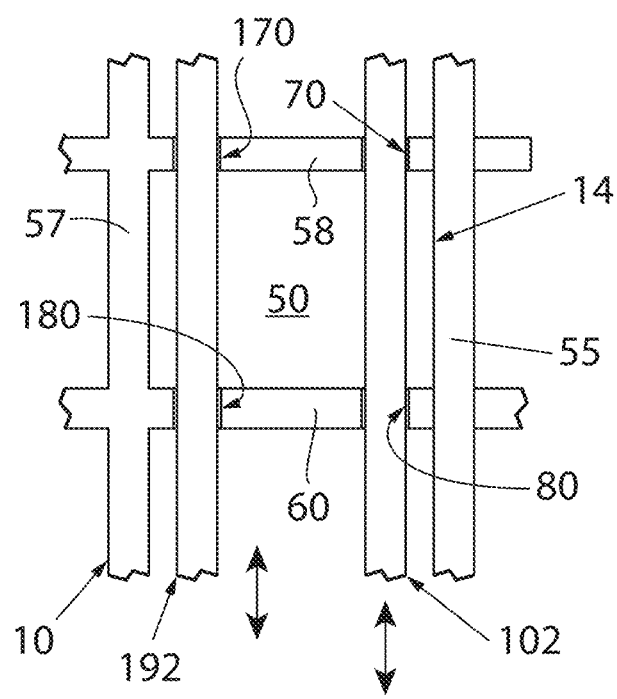
FIG. 14 is a top plan view of the system of FIG. 13.
Figure 15:
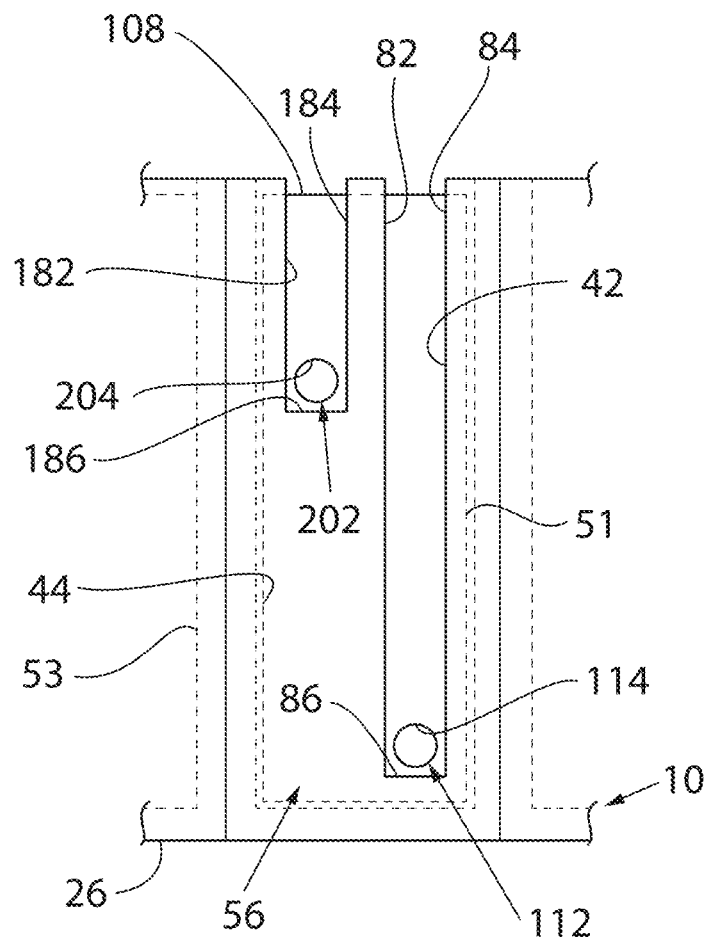
FIG. 15 is a cross-sectional view of the system of the present invention, similar to FIG. 13, showing first and second lumen models fabricated in the microwell plate.
Figure 16:
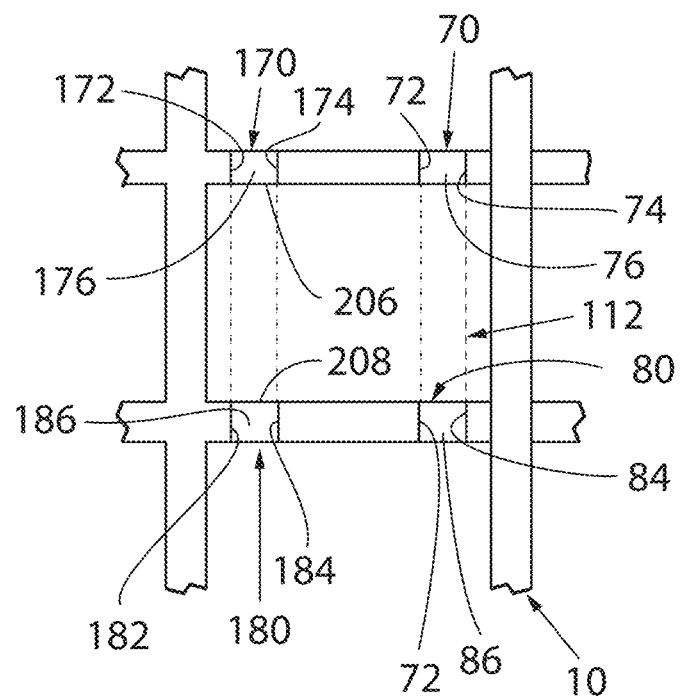
FIG. 16 is a top plan view of the system of the present invention, similar to FIG. 14, showing the first and second lumen models fabricated in the microwell plate.

In addition to supporting and moving the plurality of rods 102, as heretofore described, it is contemplated for fixture 100 to support and move a second plurality of identical, parallelly extending rods 192, as hereinafter described. It is for the second plurality of rods 192 to be magnetic to facilitate the connection of the plurality of rods 192 to fixture 100. However, the plurality of rods 192 may be fabricated from other materials without deviating from the scope of the present invention. It is contemplated for the plurality of rods 192 to lie in a common horizontal plane and be spaced from plurality of rods 102 or, as depicted in FIG. 13, to be vertically spaced from the plurality of rods 102 and to be spaced such from each other such that each rod 192 is axially aligned with a corresponding row 30a-30h of wells 14 in well plate 10. Each of the plurality of rods 192 has an outer surface 194 and a generally circular cross-section. It is intended for fixture 100 to simultaneously move the plurality of rods 102 and the second plurality of rods 192 axially from a first retracted position, shown in phantom in FIG. 1, wherein the plurality of rods 102 and the second plurality of rods 192 are removed from well plate 10, and second extended position wherein: 1) each rod 102 extends through first and second rod receiving slots 70 and 80, respectively, in third and fourth sidewalls 38 and 40, respectively, defining each well 14 in a corresponding row 30a-30h of wells 14 in well plate 10; and 2) each rod 192 extends through first and second rod receiving slots 170 and 180, respectively, in third and fourth sidewalls 38 and 40, respectively, defining each well 14 in a corresponding row 30a-30h of wells 14 in well plate 10In operation, with the plurality of rods 102 and the second plurality of wells 192 in the first retracted position, fixture 100 and well plate 10 are aligned such that each rod 102 of the plurality of rods 102 in axially aligned with first and second rod receiving slots 70 and 80, respectively, in third and fourth sidewalls 38 and 40, respectively, defining each well 14 in a corresponding row 30a-30h of wells 14 in well plate 10 and such that each rod 192 of the second plurality of rods 192 in axially aligned with first and second rod receiving slots 170 and 180, respectively, in third and fourth sidewalls 38 and 40, respectively, defining each well 14 in a corresponding row 30a-30h of wells 14 in well plate 10. Thereafter, the plurality of rods 102 and the second plurality of rods 192 are moved from the first retracted position to the second extended position wherein: 1) each rod 102 extends through first and second rod receiving slots 70 and 80, respectively, in third and fourth sidewalls 38 and 40, respectively, defining each well 14 in a corresponding row 30a-30h of wells 14 in well plate 10; and 2) each rod 192 extends through first and second rod receiving slots 170 and 180, respectively, in third and fourth sidewalls 38 and 40, respectively, defining each well 14 in a corresponding row 30a-30h of wells 14 in well plate 10.

Unpolymerized, polymerizable material 108, such as a synthetic hydrogel, is deposited into interior 50 of a portion of wells 14 in each row 30a-30h of wells 14 in well plate 10, e.g., via pipetting. For example, it is contemplated to provide unpolymerized, polymerizable material 108 in the interior 50 of well 14 at the intersection of row 30d, column 32b. Thereafter, a predetermined stimulus, e.g., heat or light, is directed at material 108 in the interior 50 of well 14 at the intersection of row 30d, column 32b such that material 108 in the interior 50 of well 14 at the intersection of row 30d, column 32b is polymerized. With material 108 in the interior 50 of well 14 at the intersection of row 30d, column 32b polymerized, fixture 100 retracts the plurality of rods 102 and the second plurality of rods 192 from the polymerized material 108 in interior 50 of well 14 at the intersection of row 30d, column 32b, such that in addition to generally tubular passageway 112 extending through polymerized material 108 extending between third and fourth sidewalls 38 and 40, respectively, a second, generally tubular passageway 202 extends through polymerized material 108 extending between third and fourth sidewalls 38 and 40, respectively. Second tubular passageway 202 is defined by tubular surface 204 of polymerized material 108 and includes a first opening 206 communicating with fifth rod receiving slot 170 in third sidewall 38 and a second opening 208 communicating with sixth rod receiving slot 180 in fourth sidewall 40.

It can be understood that a media, which may include cells, molecules or the like, may be deposited in well 14 at row 30d, column 32a, adjacent to well 14 at row 30d, column 32b, having tubular passageways 112 and 202 extending through polymerized material 108 therein. As such, the media travels through: 1) first opening 116, tubular passageway 112, second opening 118 and second rod receiving slot 80 in fourth sidewall 40 into well 14, e.g., at row 30d, column 32c, adjacent thereto by means of gravity, a mechanical device or the like; and 2) first opening 206, second tubular passageway 202, second opening 208 and fourth rod receiving slot 180 in fourth sidewall 40 into well 14 at row 30d, column 32c, adjacent thereto by means of gravity, a mechanical device or the like.

As described, it can be understood that the description of system 5 is merely exemplary and that numerous variations are possible without deviating from the scope of the present invention. For example, it can appreciated that the configuration, arrangement and number of wells 14 in well plate 10 may be varied without deviating from the scope of the present invention. Further, it can be understood that the arrangement, number and orientation of the tubular passageways through the polymerized material in the wells 14 in well plate 10 may be varied without deviating from the scope of the present invention. Likewise, it can be appreciated that the arrangement, number and orientation of the tubular passageways through the polymerized material in each wells 14 in well plate 10 may be the same or different, by altering the arrangement, number and orientation of the plurality of rods passing through each well 14 in well plate 10.

Various modes of carrying out the invention are contemplated as being within the scope of the following claims particularly pointing out and distinctly claiming the subject matter that is regarded as the invention.

We claim:

1. A device for creating a lumen in a microenvironment, comprising:
    a microwell plate defining a plurality of wells arranged in rows and columns, each of the plurality of wells defined by at least one sidewall having first and second openings therein;
    a plurality of rods, each rod selectively moveable between a first position wherein each rod is removed from corresponding first and second openings in each of the at least one sidewall defining the plurality of wells and a second position wherein each rod is inserted through the corresponding first and second openings in each of the at least one sidewall defining the plurality of wells; and
    a fixture interconnected to the plurality of rods, the fixture configured for moving the plurality of rods between the first and second positions.

2. The device of claim 1 wherein each of the plurality of rods are parallel to each other.

3. The device of claim 1 wherein:
    the at least one sidewall defining the plurality of wells has third and fourth openings therein;
    the plurality of rods is a first plurality of rods; and
    the device further includes a second plurality of rods, each rod of the second plurality of rods selectively moveable between a first position wherein each rod of the second plurality of rods is removed from the third and fourth openings in each of the at least one sidewall defining the plurality of wells and a second position wherein each rod of the second plurality of rods is inserted through the third and fourth openings in each of the at least one sidewall defining the plurality of wells.

4. The device of claim 3 wherein the fixture is interconnected to the second plurality of rods, the fixture configured for moving the second plurality of rods between the first and second positions.

5. The device of claim 3 wherein the first plurality of rods lie in a first plane and the second plurality of rods lie in a second plane spaced from the first plane.

6. The device of claim 3 wherein the fixture is a first fixture and wherein the device further comprises a second fixture interconnected to the second plurality of rods, the second fixture configured for moving the second plurality of rods between the first and second positions.

7. The device of claim 3 wherein the first plurality of rods is transverse to the second plurality of rods.

8. The device of claim 3 wherein:
   each of the first plurality of rods travels along a path between the first and second positions of the first plurality of rods;
   each of the second plurality of rods travels along a path between the first and second positions of the second plurality of rods; and
   the path of each of the first plurality of rods is interested by the paths of the second plurality of rods.

9. The device of claim 1 wherein each of the plurality of rods has a circular cross-section.

10. The device of claim 2 wherein each of the plurality of rods is magnetic.

11. The device of claim 3 wherein each of the plurality of rods is fabricated from a polymer.

\* \* \* \* \*